(12) United States Patent
Morton

(10) Patent No.: US 9,332,624 B2
(45) Date of Patent: May 3, 2016

(54) GANTRY SCANNER SYSTEMS

(71) Applicant: Rapiscan Systems, Inc., Torrance, CA (US)

(72) Inventor: Edward James Morton, Guildford (GB)

(73) Assignee: Rapiscan Systems, Inc., Torrance, CA (US)

( * ) Notice: Subject to any disclaimer, the term of this patent is extended or adjusted under 35 U.S.C. 154(b) by 150 days.

(21) Appl. No.: 14/047,619

(22) Filed: Oct. 7, 2013

(65) Prior Publication Data

US 2014/0161231 A1  Jun. 12, 2014

Related U.S. Application Data

(63) Continuation of application No. 12/993,832, filed as application No. PCT/GB2009/001277 on May 20, 2009, now Pat. No. 8,579,506.

(30) Foreign Application Priority Data

May 20, 2008  (GB) .................................. 0809110.0

(51) Int. Cl.
| | |
|---|---|
| *H05G 1/06* | (2006.01) |
| *H05G 1/10* | (2006.01) |
| *G01V 5/00* | (2006.01) |
| *G01N 23/04* | (2006.01) |

(52) U.S. Cl.
CPC .................. *H05G 1/10* (2013.01); *G01N 23/04* (2013.01); *G01V 5/0008* (2013.01); *G01V 5/0083* (2013.01)

(58) Field of Classification Search
CPC ... G01V 5/0008; G01V 5/0016; G01N 23/04; G01N 23/06; H05G 1/02; H05G 1/06; A61B 6/44; A61B 6/4405; A61B 6/4429; A61B 6/4435; A61B 6/4441
USPC ............................. 378/57, 193, 194, 197, 198
See application file for complete search history.

(56) References Cited

U.S. PATENT DOCUMENTS

| | | |
|---|---|---|
| 2,420,845 A | 5/1947 | Slack |
| 2,636,619 A | 4/1953 | Alexander |
| 2,831,123 A | 4/1958 | Daly |
| 2,885,069 A | 5/1959 | Bowen |
| 2,952,790 A | 9/1960 | Steen |
| 2,971,433 A | 2/1961 | Akin |

(Continued)

FOREIGN PATENT DOCUMENTS

| | | |
|---|---|---|
| DE | 2729353 A1 | 1/1979 |
| DE | 3214910 A1 | 5/1983 |

(Continued)

OTHER PUBLICATIONS

US 5,987,079, 11/1999, Scott (withdrawn).

(Continued)

*Primary Examiner* — Jurie Yun
(74) *Attorney, Agent, or Firm* — Novel IP

(57) ABSTRACT

A gantry scanner system comprises a radiation source, a plurality of detectors and a support frame supporting the detectors. The support frame includes an elongate support member arranged to support the detectors, cable support means arranged to support power cables or signal cables connected to the detectors, and cover means arranged to cover the support member, the cable support means and the detectors.

12 Claims, 4 Drawing Sheets

(56) References Cited

U.S. PATENT DOCUMENTS

| | | | |
|---|---|---|---|
| 3,070,399 A | 12/1962 | Bartlett |
| 3,073,960 A | 1/1963 | Guentner |
| 3,146,349 A | 8/1964 | Jordan |
| 3,239,706 A | 3/1966 | Farrell |
| 3,275,831 A | 9/1966 | Martin |
| 3,374,355 A | 3/1968 | Parratt |
| 3,458,026 A | 7/1969 | Lauzon |
| 3,485,339 A | 12/1969 | Miller |
| 3,676,783 A | 7/1972 | Kinbara |
| 3,766,387 A | 10/1973 | Heffan |
| 3,767,850 A | 10/1973 | McMillian et al. |
| 3,768,645 A | 10/1973 | Conway |
| 3,770,955 A | 11/1973 | Tomita |
| 3,784,837 A | 1/1974 | Holmstrom |
| 3,837,502 A | 9/1974 | Hornagold |
| RE28,544 E | 9/1975 | Stein |
| 3,904,923 A | 9/1975 | Schwartz |
| 3,919,467 A | 11/1975 | Peugeot |
| 3,955,678 A | 5/1976 | Moyer |
| 3,961,186 A | 6/1976 | Leunbach |
| 3,980,889 A | 9/1976 | Haas |
| 4,047,035 A | 9/1977 | Dennhoven |
| 4,057,725 A | 11/1977 | Wagner |
| 4,064,440 A | 12/1977 | Roder |
| 4,105,922 A | 8/1978 | Lambert |
| 4,139,771 A | 2/1979 | Dennhoven |
| 4,164,138 A | 8/1979 | Burkhart |
| 4,210,811 A | 7/1980 | Dennhoven |
| 4,216,499 A | 8/1980 | Dennhoven |
| 4,228,353 A | 10/1980 | Johnson |
| 4,259,721 A | 3/1981 | Kuznia |
| 4,266,425 A | 5/1981 | Allport |
| 4,274,005 A | 6/1981 | Yamamura |
| 4,340,816 A | 7/1982 | Schott |
| 4,352,021 A | 9/1982 | Boyd |
| 4,366,382 A | 12/1982 | Kotowski |
| 4,380,817 A | 4/1983 | Harding |
| 4,430,568 A | 2/1984 | Yoshida |
| 4,468,802 A | 8/1984 | Friedel |
| 4,481,403 A | 11/1984 | Del Monte |
| 4,501,011 A | 2/1985 | Hauck |
| 4,525,854 A | 6/1985 | Molbert |
| 4,563,707 A | 1/1986 | Kishida |
| 4,566,113 A | 1/1986 | Doenges |
| 4,599,740 A | 7/1986 | Cable |
| 4,626,688 A | 12/1986 | Barnes |
| 4,641,330 A | 2/1987 | Herwig |
| 4,672,649 A | 6/1987 | Rutt |
| 4,675,890 A | 6/1987 | Plessis |
| 4,709,382 A | 11/1987 | Sones |
| 4,736,401 A | 4/1988 | Donges |
| 4,752,948 A | 6/1988 | MacMahon |
| 4,788,704 A | 11/1988 | Donges |
| 4,799,247 A | 1/1989 | Annis |
| 4,809,857 A | 3/1989 | Steuck |
| 4,817,123 A | 3/1989 | Sones |
| 4,825,454 A | 4/1989 | Annis |
| 4,831,260 A | 5/1989 | DiBianca |
| RE32,961 E | 6/1989 | Wagner |
| 4,853,595 A | 8/1989 | Alfano |
| 4,864,142 A | 9/1989 | Gomberg |
| 4,866,439 A | 9/1989 | Kraus |
| 4,866,745 A | 9/1989 | Akai |
| 4,868,856 A | 9/1989 | Frith |
| 4,870,670 A | 9/1989 | Geus |
| 4,872,188 A | 10/1989 | Lauro |
| 4,879,735 A | 11/1989 | Owens |
| 4,884,289 A | 11/1989 | Glockmann |
| 4,887,604 A | 12/1989 | Shefer |
| 4,979,137 A | 12/1990 | Gerstenfeld |
| 4,979,202 A | 12/1990 | Siczek |
| 4,987,584 A | 1/1991 | Doenges |
| 4,991,189 A | 2/1991 | Boomgaarden |
| 4,991,708 A | 2/1991 | Francioni |
| 5,006,299 A | 4/1991 | Gozani |
| 5,014,293 A | 5/1991 | Boyd |
| 5,022,062 A | 6/1991 | Annis |
| 5,033,106 A | 7/1991 | Kita |
| 5,040,199 A | 8/1991 | Stein |
| 5,065,418 A | 11/1991 | Bermbach |
| 5,067,145 A | 11/1991 | Siczek |
| 5,076,993 A | 12/1991 | Sawa |
| 5,086,300 A | 2/1992 | Ashmore |
| 5,091,924 A | 2/1992 | Bermbach |
| 5,092,451 A | 3/1992 | Jones |
| 5,097,939 A | 3/1992 | Shanklin |
| 5,098,640 A | 3/1992 | Gozani |
| 5,114,662 A | 5/1992 | Gozani |
| 5,144,191 A | 9/1992 | Jones |
| 5,179,581 A | 1/1993 | Annis |
| 5,181,234 A | 1/1993 | Smith |
| 5,182,764 A | 1/1993 | Peschmann |
| 5,185,778 A | 2/1993 | Magram |
| 5,202,932 A | 4/1993 | Cambier |
| 5,221,843 A | 6/1993 | Alvarez |
| 5,224,144 A | 6/1993 | Annis |
| 5,237,598 A | 8/1993 | Albert |
| 5,243,693 A | 9/1993 | Maron |
| 5,247,556 A | 9/1993 | Eckert |
| 5,247,561 A | 9/1993 | Kotowski |
| 5,253,283 A | 10/1993 | Annis |
| 5,259,014 A | 11/1993 | Brettschneider |
| 5,260,983 A | 11/1993 | Ono |
| 5,272,627 A | 12/1993 | Maschhoff |
| 5,313,511 A | 5/1994 | Annis |
| 5,319,547 A | 6/1994 | Krug |
| 5,321,271 A | 6/1994 | Schonberg |
| 5,341,916 A | 8/1994 | Doane |
| 5,367,552 A | 11/1994 | Peschmann |
| 5,379,334 A | 1/1995 | Zimmer |
| 5,394,454 A | 2/1995 | Harding |
| 5,410,156 A | 4/1995 | Miller |
| 5,412,702 A | 5/1995 | Sata |
| 5,418,372 A | 5/1995 | Schonberg |
| 5,430,787 A | 7/1995 | Norton |
| 5,467,377 A | 11/1995 | Dawson |
| 5,490,196 A | 2/1996 | Rudich |
| 5,490,218 A | 2/1996 | Krug |
| 5,493,596 A | 2/1996 | Annis |
| 5,505,291 A | 4/1996 | Huang |
| 5,511,104 A | 4/1996 | Mueller |
| 5,524,133 A | 6/1996 | Neale |
| 5,548,123 A | 8/1996 | Perez-Mendez |
| 5,557,108 A | 9/1996 | Tumer |
| 5,590,057 A | 12/1996 | Fletcher |
| 5,600,303 A | 2/1997 | Husseiny |
| 5,600,700 A | 2/1997 | Krug |
| 5,604,778 A | 2/1997 | Polacin |
| 5,606,167 A | 2/1997 | Miller |
| 5,633,907 A | 5/1997 | Gravelle |
| 5,634,551 A | 6/1997 | Francioni |
| 5,638,420 A | 6/1997 | Armistead |
| 5,638,817 A * | 6/1997 | Morgan et al. ............... 600/425 |
| 5,642,393 A | 6/1997 | Krug |
| 5,642,394 A | 6/1997 | Rothschild |
| 5,660,549 A | 8/1997 | Witt |
| 5,661,377 A | 8/1997 | Mishin |
| 5,661,774 A | 8/1997 | Gordon |
| 5,666,393 A | 9/1997 | Annis |
| 5,687,210 A | 11/1997 | Maitrejean |
| 5,689,541 A | 11/1997 | Schardt |
| 5,692,028 A | 11/1997 | Geus |
| 5,692,029 A | 11/1997 | Husseiny |
| 5,696,806 A | 12/1997 | Grodzins |
| 5,712,926 A | 1/1998 | Eberhard |
| 5,738,202 A | 4/1998 | Ydoate |
| 5,744,919 A | 4/1998 | Mishin |
| 5,751,837 A | 5/1998 | Watanabe |
| 5,763,886 A | 6/1998 | Schulte |
| 5,764,683 A | 6/1998 | Swift |
| 5,768,334 A | 6/1998 | Maitrejean |
| 5,787,145 A | 7/1998 | Geus |
| 5,796,802 A | 8/1998 | Gordon |
| 5,805,660 A | 9/1998 | Perion |

(56) References Cited

U.S. PATENT DOCUMENTS

| | | |
|---|---|---|
| 5,818,897 A | 10/1998 | Gordon |
| 5,838,758 A | 11/1998 | Krug |
| 5,838,759 A | 11/1998 | Armistead |
| 5,841,831 A | 11/1998 | Hell |
| 5,859,891 A | 1/1999 | Hibbard |
| 5,870,449 A | 2/1999 | Lee |
| 5,881,122 A | 3/1999 | Crawford |
| 5,882,206 A | 3/1999 | Gillio |
| 5,887,047 A | 3/1999 | Bailey |
| 5,901,198 A | 5/1999 | Crawford |
| 5,903,623 A | 5/1999 | Swift |
| 5,905,806 A | 5/1999 | Eberhard |
| 5,909,477 A | 6/1999 | Crawford |
| 5,909,478 A | 6/1999 | Polichar |
| 5,910,973 A | 6/1999 | Grodzins |
| 5,930,326 A | 7/1999 | Rothschild |
| 5,940,468 A | 8/1999 | Huang |
| 5,949,811 A | 9/1999 | Baba |
| 5,949,842 A | 9/1999 | Schafer |
| 5,963,211 A | 10/1999 | Oikawa |
| 5,966,422 A | 10/1999 | Dafni |
| 5,970,113 A | 10/1999 | Crawford |
| 5,974,111 A | 10/1999 | Krug |
| 5,982,843 A | 11/1999 | Bailey |
| 5,987,097 A | 11/1999 | Salasoo |
| 6,018,562 A | 1/2000 | Willson |
| 6,021,174 A | 2/2000 | Campbell |
| 6,026,143 A | 2/2000 | Simanovsky |
| 6,026,171 A | 2/2000 | Hiraoglu |
| 6,031,888 A * | 2/2000 | Ivan et al. ................. 378/20 |
| 6,031,890 A | 2/2000 | Bermbach |
| 6,032,808 A | 3/2000 | Henson |
| 6,035,014 A | 3/2000 | Hiraoglu |
| 6,037,597 A | 3/2000 | Karavolos |
| 6,044,353 A | 3/2000 | Pugliese |
| 6,056,671 A | 5/2000 | Marmer |
| 6,058,158 A | 5/2000 | Eiler |
| 6,067,344 A | 5/2000 | Grodzins |
| 6,067,366 A | 5/2000 | Simanovsky |
| 6,073,751 A | 6/2000 | Worzischek |
| 6,075,871 A | 6/2000 | Simanovsky |
| 6,076,400 A | 6/2000 | Bechwati |
| 6,078,642 A | 6/2000 | Simanovsky |
| 6,081,580 A | 6/2000 | Grodzins |
| 6,088,423 A | 7/2000 | Krug |
| 6,091,795 A | 7/2000 | Schafer |
| 6,094,472 A | 7/2000 | Smith |
| 6,108,396 A | 8/2000 | Bechwati |
| 6,111,974 A | 8/2000 | Hiraoglu |
| 6,118,852 A | 9/2000 | Rogers |
| 6,122,343 A | 9/2000 | Pidcock |
| 6,128,365 A | 10/2000 | Bechwati |
| 6,134,299 A | 10/2000 | Artig |
| 6,137,895 A | 10/2000 | Al-Sheikh |
| 6,149,592 A | 11/2000 | Yanof |
| 6,151,381 A | 11/2000 | Grodzins |
| 6,163,591 A | 12/2000 | Benjamin |
| 6,181,765 B1 | 1/2001 | Sribar |
| 6,183,139 B1 | 2/2001 | Solomon |
| 6,185,272 B1 | 2/2001 | Hiraoglu |
| 6,188,745 B1 | 2/2001 | Gordon |
| 6,188,747 B1 | 2/2001 | Geus |
| 6,192,101 B1 | 2/2001 | Grodzins |
| 6,192,104 B1 | 2/2001 | Adams |
| 6,195,413 B1 | 2/2001 | Geus |
| 6,195,444 B1 | 2/2001 | Simanovsky |
| 6,198,795 B1 | 3/2001 | Naumann |
| 6,200,024 B1 | 3/2001 | Negrelli |
| 6,212,251 B1 | 4/2001 | Tomura |
| 6,216,540 B1 | 4/2001 | Nelson |
| 6,218,943 B1 | 4/2001 | Ellenbogen |
| 6,236,709 B1 | 5/2001 | Perry |
| 6,236,712 B1 | 5/2001 | Tomasetti |
| 6,246,320 B1 | 6/2001 | Monroe |
| 6,249,567 B1 | 6/2001 | Rothschild |
| 6,252,929 B1 | 6/2001 | Swift |
| 6,256,369 B1 | 7/2001 | Lai |
| 6,256,404 B1 | 7/2001 | Gordon |
| 6,269,142 B1 | 7/2001 | Smith |
| 6,272,230 B1 | 8/2001 | Hiraoglu |
| 6,278,115 B1 | 8/2001 | Annis |
| 6,282,260 B1 | 8/2001 | Grodzins |
| 6,292,533 B1 | 9/2001 | Swift |
| 6,301,326 B2 | 10/2001 | Bjorkholm |
| 6,301,327 B1 | 10/2001 | Martens |
| 6,304,629 B1 | 10/2001 | Conway |
| 6,317,509 B1 | 11/2001 | Simanovsky |
| 6,320,933 B1 | 11/2001 | Grodzins |
| 6,324,249 B1 | 11/2001 | Fazzio |
| 6,345,113 B1 | 2/2002 | Crawford |
| 6,347,132 B1 | 2/2002 | Annis |
| 6,356,620 B1 | 3/2002 | Rothschild |
| 6,396,899 B2 | 5/2002 | Kuwabara |
| 6,418,189 B1 | 7/2002 | Schafer |
| 6,418,194 B1 | 7/2002 | McPherson |
| 6,421,420 B1 | 7/2002 | Grodzins |
| 6,424,695 B1 | 7/2002 | Grodzins |
| 6,427,891 B1 | 8/2002 | Anderson |
| 6,429,578 B1 | 8/2002 | Danielsson |
| 6,430,255 B2 | 8/2002 | Fenkart |
| 6,431,344 B1 | 8/2002 | Emmermann |
| 6,434,219 B1 | 8/2002 | Rothschild |
| 6,435,715 B1 | 8/2002 | Betz |
| 6,438,201 B1 | 8/2002 | Mazess |
| 6,442,233 B1 | 8/2002 | Grodzins |
| 6,445,765 B1 | 9/2002 | Frank |
| 6,446,782 B1 | 9/2002 | Patrick |
| 6,448,564 B1 | 9/2002 | Johnson |
| 6,453,003 B1 | 9/2002 | Springer |
| 6,453,007 B2 | 9/2002 | Adams |
| 6,456,684 B1 | 9/2002 | Mun |
| 6,459,755 B1 | 10/2002 | Li |
| 6,459,761 B1 | 10/2002 | Grodzins |
| 6,459,764 B1 | 10/2002 | Chalmers |
| 6,473,487 B1 | 10/2002 | Le |
| RE37,899 E | 11/2002 | Grodzins |
| 6,483,894 B2 | 11/2002 | Hartick |
| 6,507,025 B1 | 1/2003 | Verbinski |
| 6,528,787 B2 | 3/2003 | Katagami |
| 6,532,276 B1 | 3/2003 | Hartick |
| 6,542,574 B2 | 4/2003 | Grodzins |
| 6,542,578 B2 | 4/2003 | Ries |
| 6,542,580 B1 | 4/2003 | Carver |
| 6,543,599 B2 | 4/2003 | Jasinetzky |
| 6,546,072 B1 | 4/2003 | Chalmers |
| 6,552,346 B2 | 4/2003 | Verbinski |
| 6,556,653 B2 | 4/2003 | Hussein |
| 6,563,903 B2 | 5/2003 | Kang |
| 6,563,906 B2 | 5/2003 | Hussein |
| 6,567,496 B1 | 5/2003 | Sychev |
| 6,580,778 B2 | 6/2003 | Meder |
| 6,584,170 B2 | 6/2003 | Aust |
| 6,590,956 B2 | 7/2003 | Fenkart |
| 6,591,130 B2 | 7/2003 | Shahidi |
| 6,597,760 B2 | 7/2003 | Beneke |
| 6,606,516 B2 | 8/2003 | Levine |
| 6,618,466 B1 | 9/2003 | Ning |
| 6,621,888 B2 | 9/2003 | Grodzins |
| 6,629,593 B2 | 10/2003 | Zeitler |
| 6,636,581 B2 | 10/2003 | Sorenson |
| 6,636,623 B2 | 10/2003 | Nelson |
| 6,647,091 B2 | 11/2003 | Fenkart |
| 6,647,094 B2 | 11/2003 | Harding |
| 6,647,095 B2 | 11/2003 | Hsieh |
| 6,653,588 B1 | 11/2003 | Gillard-Hickman |
| 6,658,087 B2 | 12/2003 | Chalmers |
| 6,661,867 B2 | 12/2003 | Mario |
| 6,661,876 B2 | 12/2003 | Turner |
| 6,663,280 B2 | 12/2003 | Doenges |
| 6,665,373 B1 | 12/2003 | Kotowski |
| 6,665,433 B2 | 12/2003 | Roder |
| 6,687,333 B2 | 2/2004 | Carroll |
| 6,690,766 B2 | 2/2004 | Kresse |
| 6,707,879 B2 | 3/2004 | McClelland |

(56) References Cited

U.S. PATENT DOCUMENTS

| | | |
|---|---|---|
| 6,713,773 B1 | 3/2004 | Lyons |
| 6,715,533 B2 | 4/2004 | Kresse |
| 6,721,387 B1 | 4/2004 | Naidu |
| 6,721,391 B2 | 4/2004 | McClelland |
| 6,727,506 B2 | 4/2004 | Mallette |
| 6,735,271 B1 | 5/2004 | Rand |
| 6,737,652 B2 | 5/2004 | Lanza |
| 6,744,845 B2 | 6/2004 | Harding |
| 6,748,043 B1 | 6/2004 | Dobbs |
| 6,754,298 B2 | 6/2004 | Fessler |
| 6,760,407 B2 | 7/2004 | Price |
| 6,763,083 B2 | 7/2004 | Fernandez |
| 6,763,635 B1 | 7/2004 | Lowman |
| 6,770,884 B2 | 8/2004 | Bryman |
| 6,775,348 B2 | 8/2004 | Hoffman |
| 6,785,357 B2 | 8/2004 | Bernardi |
| 6,788,761 B2 | 9/2004 | Bijjani |
| 6,812,426 B1 | 11/2004 | Kotowski |
| 6,813,374 B1 | 11/2004 | Karimi |
| 6,816,571 B2 | 11/2004 | Bijjani |
| 6,827,265 B2 | 12/2004 | Knowles |
| 6,829,585 B1 | 12/2004 | Grewal |
| 6,830,185 B2 | 12/2004 | Tsikos |
| 6,837,422 B1 | 1/2005 | Meder |
| 6,837,432 B2 | 1/2005 | Tsikos |
| 6,839,134 B2 | 1/2005 | Saito |
| 6,839,403 B1 | 1/2005 | Kotowski |
| 6,843,599 B2 | 1/2005 | Le |
| 6,856,344 B2 | 2/2005 | Frantz |
| 6,856,667 B2 | 2/2005 | Ellenbogen |
| 6,859,514 B2 | 2/2005 | Hoffman |
| 6,869,217 B2 | 3/2005 | Rasche |
| 6,876,719 B2 | 4/2005 | Ozaki |
| 6,876,724 B2 | 4/2005 | Zhou |
| 6,879,657 B2 | 4/2005 | Hoffman |
| 6,899,540 B1 | 5/2005 | Neiderman |
| 6,901,135 B2 | 5/2005 | Fox |
| 6,901,346 B2 | 5/2005 | Tracy |
| 6,906,329 B2 | 6/2005 | Bryman |
| 6,907,101 B2 | 6/2005 | Hoffman |
| 6,920,197 B2 | 7/2005 | Kang |
| 6,922,455 B2 | 7/2005 | Jurczyk |
| 6,922,460 B2 | 7/2005 | Skatter |
| 6,922,461 B2 | 7/2005 | Kang |
| 6,928,141 B2 | 8/2005 | Carver |
| 6,933,504 B2 | 8/2005 | Hoffman |
| 6,934,354 B2 | 8/2005 | Hoffman |
| 6,937,692 B2 | 8/2005 | Johnson |
| 6,940,071 B2 | 9/2005 | Ramsden |
| 6,944,264 B2 | 9/2005 | Bijjani |
| 6,947,517 B2 | 9/2005 | Hoffman |
| 6,950,492 B2 | 9/2005 | Besson |
| 6,950,493 B2 | 9/2005 | Besson |
| 6,952,163 B2 | 10/2005 | Huey |
| 6,953,935 B1 | 10/2005 | Hoffman |
| 6,957,913 B2 | 10/2005 | Renkart |
| 6,962,289 B2 | 11/2005 | Vatan |
| 6,965,314 B2 | 11/2005 | Bohinc, Jr. |
| 6,968,030 B2 | 11/2005 | Hoffman |
| 6,968,034 B2 | 11/2005 | Ellenbogen |
| 6,971,577 B2 | 12/2005 | Tsikos |
| 6,972,693 B2 | 12/2005 | Brown |
| 6,973,158 B2 | 12/2005 | Besson |
| 6,975,698 B2 | 12/2005 | Katcha |
| 6,978,936 B2 | 12/2005 | Tsikos |
| 6,980,627 B2 | 12/2005 | Qiu |
| 6,990,171 B2 | 1/2006 | Toth |
| 6,990,172 B2 | 1/2006 | Toth |
| 6,991,371 B2 | 1/2006 | Georgeson |
| 6,993,115 B2 | 1/2006 | McGuire |
| 6,996,209 B2 | 2/2006 | Marek |
| 7,010,083 B2 | 3/2006 | Hoffman |
| 7,010,094 B2 | 3/2006 | Grodzins |
| 7,016,459 B2 | 3/2006 | Ellenbogen |
| 7,020,241 B2 | 3/2006 | Beneke |
| 7,020,242 B2 | 3/2006 | Ellenbogen |
| 7,023,956 B2 | 4/2006 | Heaton |
| 7,023,957 B2 | 4/2006 | Bijjani |
| 7,027,553 B2 | 4/2006 | Dunham |
| 7,027,554 B2 | 4/2006 | Gaultier |
| 7,028,442 B2 | 4/2006 | Merrifield |
| 7,031,430 B2 | 4/2006 | Kaucic |
| 7,031,434 B1 | 4/2006 | Saunders |
| 7,034,313 B2 | 4/2006 | Hoffman |
| 7,039,154 B1 | 5/2006 | Ellenbogen |
| 7,039,159 B2 | 5/2006 | Muenchau |
| 7,042,975 B2 | 5/2006 | Heuscher |
| 7,045,787 B1 | 5/2006 | Verbinski |
| 7,045,788 B2 | 5/2006 | Iwatschenko-Borho |
| 7,046,756 B2 | 5/2006 | Hoffman |
| 7,046,761 B2 | 5/2006 | Ellenbogen |
| 7,046,768 B1 | 5/2006 | Gilevich |
| 7,050,536 B1 | 5/2006 | Fenkart |
| 7,050,541 B2 | 5/2006 | Bittl |
| 7,054,408 B2 | 5/2006 | Jiang |
| 7,062,009 B2 | 6/2006 | Karimi |
| 7,062,011 B1 | 6/2006 | Tybinkowski |
| 7,062,074 B1 | 6/2006 | Beneke |
| 7,064,334 B2 | 6/2006 | Hoffman |
| 7,065,175 B2 | 6/2006 | Green |
| 7,065,179 B2 | 6/2006 | Block |
| 7,068,749 B2 | 6/2006 | Kollegal |
| 7,068,750 B2 | 6/2006 | Toth |
| 7,068,751 B2 | 6/2006 | Toth |
| 7,072,434 B1 | 7/2006 | Tybinkowski |
| 7,076,029 B2 | 7/2006 | Toth |
| 7,078,699 B2 | 7/2006 | Seppi |
| 7,081,628 B2 | 7/2006 | Granfors |
| 7,084,404 B2 | 8/2006 | Hoffman |
| 7,087,902 B2 | 8/2006 | Wang |
| 7,088,799 B2 | 8/2006 | Hoffman |
| 7,090,133 B2 | 8/2006 | Zhu |
| 7,092,481 B2 | 8/2006 | Hoffman |
| 7,092,485 B2 | 8/2006 | Kravis |
| 7,099,434 B2 | 8/2006 | Adams |
| 7,099,435 B2 | 8/2006 | Heumann |
| 7,103,137 B2 | 9/2006 | Seppi |
| 7,110,488 B2 | 9/2006 | Katcha |
| 7,112,797 B2 | 9/2006 | Hoge |
| 7,116,235 B2 | 10/2006 | Alioto |
| 7,116,749 B2 | 10/2006 | Besson |
| 7,116,751 B2 | 10/2006 | Ellenbogen |
| 7,119,553 B2 | 10/2006 | Yang |
| 7,123,681 B2 | 10/2006 | Ellenbogen |
| 7,127,027 B2 | 10/2006 | Hoffman |
| 7,130,374 B1 | 10/2006 | Jacobs |
| RE39,396 E | 11/2006 | Swift |
| 7,133,491 B2 | 11/2006 | Bernardi |
| 7,136,450 B2 | 11/2006 | Ying |
| 7,136,451 B2 | 11/2006 | Naidu |
| 7,139,367 B1 | 11/2006 | Le |
| 7,139,406 B2 | 11/2006 | McClelland |
| 7,142,208 B2 | 11/2006 | Lorenz |
| 7,142,629 B2 | 11/2006 | Edic |
| 7,149,278 B2 | 12/2006 | Arenson |
| 7,149,339 B2 | 12/2006 | Veneruso |
| 7,154,989 B2 * | 12/2006 | Ueno et al. .................... 378/19 |
| 7,155,812 B1 | 1/2007 | Peterson |
| 7,158,611 B2 | 1/2007 | Heismann |
| 7,162,005 B2 | 1/2007 | Bjorkholm |
| 7,162,285 B2 | 1/2007 | Owens |
| 7,164,747 B2 | 1/2007 | Ellenbogen |
| 7,164,750 B2 | 1/2007 | Nabors |
| 7,166,458 B2 | 1/2007 | Ballerstadt |
| 7,166,844 B1 | 1/2007 | Gormley |
| 7,167,539 B1 | 1/2007 | Hoffman |
| 7,173,998 B2 | 2/2007 | Hoffman |
| 7,177,387 B2 | 2/2007 | Yasunaga |
| 7,177,391 B2 | 2/2007 | Chapin |
| 7,187,756 B2 | 3/2007 | Gohno |
| 7,190,757 B2 | 3/2007 | Ying |
| 7,192,031 B2 | 3/2007 | Dunham |
| 7,197,113 B1 | 3/2007 | Katcha |
| 7,197,172 B1 | 3/2007 | Naidu |

(56) References Cited

U.S. PATENT DOCUMENTS

| | | |
|---|---|---|
| 7,203,276 B2 | 4/2007 | Arsenault |
| 7,203,629 B2 | 4/2007 | Oezis |
| 7,204,125 B2 | 4/2007 | Fine |
| 7,206,379 B2 | 4/2007 | Lemaitre |
| 7,207,713 B2 | 4/2007 | Lowman |
| 7,212,113 B2 | 5/2007 | Zanovitch |
| 7,215,731 B1 | 5/2007 | Basu |
| 7,215,737 B2 | 5/2007 | Li |
| 7,215,738 B2 | 5/2007 | Muenchau |
| 7,218,700 B2 | 5/2007 | Huber |
| 7,218,704 B1 | 5/2007 | Adams |
| 7,224,763 B2 | 5/2007 | Naidu |
| 7,224,765 B2 | 5/2007 | Ellenbogen |
| 7,224,766 B2 | 5/2007 | Jiang |
| 7,224,769 B2 | 5/2007 | Turner |
| 7,233,640 B2 | 6/2007 | Ikhlef |
| 7,236,564 B2 | 6/2007 | Hopkins |
| 7,238,945 B2 | 7/2007 | Hoffman |
| 7,238,951 B2 | 7/2007 | Disdier |
| 7,244,947 B2 | 7/2007 | Polichar |
| 7,247,856 B2 | 7/2007 | Hoge |
| 7,250,940 B2 | 7/2007 | Jayanetti |
| 7,251,310 B2 | 7/2007 | Smith |
| 7,257,189 B2 | 8/2007 | Modica |
| 7,260,170 B2 | 8/2007 | Arenson |
| 7,260,171 B1 | 8/2007 | Arenson |
| 7,260,172 B2 | 8/2007 | Arenson |
| 7,260,173 B2 | 8/2007 | Wakayama |
| 7,260,174 B2 | 8/2007 | Hoffman |
| 7,260,182 B2 | 8/2007 | Toth |
| 7,260,255 B2 | 8/2007 | Polichar |
| 7,263,160 B2 | 8/2007 | Schlomka |
| 7,266,180 B1 | 9/2007 | Saunders |
| 7,272,208 B2 | 9/2007 | Yatsenko |
| 7,272,429 B2 | 9/2007 | Walker |
| 7,274,767 B2 | 9/2007 | Clayton |
| 7,277,577 B2 | 10/2007 | Ying |
| 7,279,120 B2 | 10/2007 | Cheng |
| 7,280,631 B2 | 10/2007 | De |
| 7,282,727 B2 | 10/2007 | Retsky |
| 7,283,604 B2 | 10/2007 | De |
| 7,283,609 B2 | 10/2007 | Possin |
| 7,295,019 B2 | 11/2007 | Yang |
| 7,295,651 B2 | 11/2007 | Delgado |
| 7,298,812 B2 | 11/2007 | Tkaczyk |
| 7,302,083 B2 | 11/2007 | Larson |
| 7,308,073 B2 | 12/2007 | Tkaczyk |
| 7,308,074 B2 | 12/2007 | Jiang |
| 7,308,076 B2 | 12/2007 | Studer |
| 7,308,077 B2 | 12/2007 | Bijjani |
| 7,317,195 B2 | 1/2008 | Eikman |
| 7,317,259 B2 | 1/2008 | Yamauchi |
| 7,317,390 B2 | 1/2008 | Huey |
| 7,319,737 B2 | 1/2008 | Singh |
| 7,322,745 B2 | 1/2008 | Agrawal |
| 7,324,625 B2 | 1/2008 | Eilbert |
| 7,327,853 B2 | 2/2008 | Ying |
| 7,330,527 B2 | 2/2008 | Hoffman |
| 7,330,535 B2 | 2/2008 | Arenson |
| 7,333,587 B2 | 2/2008 | De |
| 7,333,588 B2 | 2/2008 | Mistretta |
| 7,333,589 B2 | 2/2008 | Ellenbogen |
| 7,335,887 B1 | 2/2008 | Verbinski |
| 7,336,769 B2 | 2/2008 | Arenson |
| 7,349,525 B2 | 3/2008 | Morton |
| 7,352,843 B2 | 4/2008 | Hu |
| 7,356,174 B2 | 4/2008 | Leue |
| 7,369,463 B1 | 5/2008 | Van Dullemen |
| 7,369,640 B2 | 5/2008 | Seppi |
| 7,369,643 B2 | 5/2008 | Kotowski |
| 7,372,040 B2 | 5/2008 | Polichar |
| 7,372,944 B2 | 5/2008 | Bernhardt |
| 7,379,530 B2 | 5/2008 | Hoff |
| 7,386,092 B2 | 6/2008 | Kang |
| 7,397,891 B2 | 7/2008 | Johnson |
| 7,400,701 B1 | 7/2008 | Cason |
| 7,420,174 B2 | 9/2008 | Kurita |
| 7,429,738 B2 | 9/2008 | Li |
| 7,440,543 B2 | 10/2008 | Morton |
| 7,453,987 B1 | 11/2008 | Richardson |
| 7,460,639 B2 | 12/2008 | Tudor |
| 7,470,914 B2 | 12/2008 | Li |
| 7,475,428 B2 | 1/2009 | Smith |
| 7,475,866 B2 | 1/2009 | Hu |
| 7,483,510 B2 | 1/2009 | Carver |
| 7,483,511 B2 | 1/2009 | Bendahan |
| 7,486,768 B2 * | 2/2009 | Allman et al. .................. 378/57 |
| 7,492,855 B2 | 2/2009 | Hopkins |
| 7,500,931 B2 | 3/2009 | Rosemeier |
| 7,505,556 B2 | 3/2009 | Chalmers |
| 7,505,557 B2 | 3/2009 | Modica |
| 7,505,562 B2 | 3/2009 | Dinca |
| 7,512,215 B2 | 3/2009 | Morton |
| 7,517,149 B2 | 4/2009 | Agrawal |
| 7,519,148 B2 | 4/2009 | Kotowski |
| 7,525,101 B2 | 4/2009 | Grodzins |
| 7,526,064 B2 | 4/2009 | Akery |
| 7,538,325 B2 | 5/2009 | Mishin |
| 7,547,888 B2 | 6/2009 | Cooke |
| 7,551,714 B2 | 6/2009 | Rothschild |
| 7,551,715 B2 | 6/2009 | Rothschild |
| 7,551,718 B2 | 6/2009 | Rothschild |
| 7,555,099 B2 | 6/2009 | Rothschild |
| 7,564,939 B2 | 7/2009 | Morton |
| 7,580,505 B2 | 8/2009 | Kang |
| 7,593,506 B2 | 9/2009 | Cason |
| 7,593,510 B2 | 9/2009 | Rothschild |
| 7,649,976 B2 | 1/2010 | Georgeson |
| 7,663,109 B2 | 2/2010 | Kang |
| 7,684,538 B2 | 3/2010 | Morton |
| 7,720,195 B2 | 5/2010 | Allman |
| 7,724,869 B2 | 5/2010 | Wang |
| 7,734,066 B2 | 6/2010 | Delia |
| 7,738,687 B2 | 6/2010 | Tortora |
| 7,741,612 B2 | 6/2010 | Clothier |
| 7,742,568 B2 | 6/2010 | Smith |
| 7,760,103 B2 | 7/2010 | Frank |
| 7,762,760 B2 | 7/2010 | Takehara |
| 7,769,133 B2 | 8/2010 | Carver |
| 7,783,003 B2 | 8/2010 | Clayton |
| 7,783,004 B2 | 8/2010 | Kotowski |
| 7,796,734 B2 | 9/2010 | Mastronardi |
| 7,800,073 B2 | 9/2010 | Clothier |
| 7,809,104 B2 | 10/2010 | Foland |
| 7,809,109 B2 | 10/2010 | Mastronardi |
| 7,817,775 B2 | 10/2010 | Kang |
| 7,817,776 B2 | 10/2010 | Agrawal |
| 7,835,486 B2 | 11/2010 | Basu |
| 7,860,213 B2 | 12/2010 | Akery |
| 7,876,879 B2 | 1/2011 | Morton |
| 7,876,880 B2 | 1/2011 | Kotowski |
| 7,885,375 B2 | 2/2011 | Bernard |
| 7,903,783 B2 | 3/2011 | Modica |
| 7,952,079 B2 | 5/2011 | Neustadter |
| 7,957,506 B2 | 6/2011 | Smith |
| 7,963,695 B2 | 6/2011 | Kotowski |
| 7,965,695 B2 | 6/2011 | Valko |
| 7,973,697 B2 | 7/2011 | Reilly |
| 7,991,113 B2 | 8/2011 | Carver |
| 7,991,117 B2 | 8/2011 | Chen |
| 7,995,705 B2 | 8/2011 | Allman |
| 8,000,436 B2 | 8/2011 | Seppi |
| 8,031,903 B2 | 10/2011 | Paresi |
| 8,059,781 B2 | 11/2011 | Agrawal |
| 8,148,693 B2 | 4/2012 | Ryge |
| 8,170,177 B2 | 5/2012 | Akery |
| 8,173,970 B2 | 5/2012 | Inbar |
| 8,194,822 B2 | 6/2012 | Rothschild |
| 8,263,938 B2 | 9/2012 | Bjorkholm |
| 8,275,091 B2 | 9/2012 | Morton |
| 8,350,747 B2 | 1/2013 | Delia |
| 8,356,937 B2 | 1/2013 | Kotowski |
| 8,385,501 B2 | 2/2013 | Allman |
| 8,389,941 B2 | 3/2013 | Bendahan |

(56) References Cited

U.S. PATENT DOCUMENTS

| | | |
|---|---|---|
| 8,389,942 B2 | 3/2013 | Morton |
| 8,401,147 B2 | 3/2013 | Ryge |
| 8,433,036 B2 | 4/2013 | Morton |
| 8,437,448 B2 | 5/2013 | Langeveld |
| 8,451,974 B2 | 5/2013 | Morton |
| 8,457,275 B2 | 6/2013 | Akery |
| 8,483,356 B2 | 7/2013 | Bendahan |
| 8,491,189 B2 | 7/2013 | Kotowski |
| 8,498,376 B2 | 7/2013 | Modica |
| 8,502,699 B2 | 8/2013 | Zerwekh |
| 8,503,605 B2 | 8/2013 | Morton |
| 8,579,506 B2 | 11/2013 | Morton |
| 8,582,720 B2 | 11/2013 | Morton |
| 8,644,453 B2 | 2/2014 | Morton |
| 8,668,386 B2 | 3/2014 | Morton |
| 8,687,765 B2 | 4/2014 | Kotowski |
| 8,735,833 B2 | 5/2014 | Morto |
| 8,744,033 B2 | 6/2014 | Oosaka |
| 8,798,232 B2 | 8/2014 | Bendahan |
| 8,831,176 B2 | 9/2014 | Morton |
| 8,837,670 B2 | 9/2014 | Akery |
| 2002/0031202 A1 | 3/2002 | Callerame |
| 2002/0038753 A1 | 4/2002 | Ursu |
| 2002/0045152 A1 | 4/2002 | Viscardi |
| 2003/0023592 A1 | 1/2003 | Modica |
| 2003/0085163 A1 | 5/2003 | Chan |
| 2004/0017888 A1 | 1/2004 | Seppi |
| 2004/0086078 A1 | 5/2004 | Adams |
| 2004/0101098 A1 | 5/2004 | Bijjani |
| 2004/0125914 A1 | 7/2004 | Kang |
| 2004/0141584 A1 | 7/2004 | Bernardi |
| 2004/0178339 A1 | 9/2004 | Gentile |
| 2004/0213378 A1 | 10/2004 | Zhou |
| 2004/0258198 A1 | 12/2004 | Carver |
| 2004/0258305 A1 | 12/2004 | Burnham |
| 2005/0008119 A1 | 1/2005 | McClelland |
| 2005/0023479 A1 | 2/2005 | Grodzins |
| 2005/0031076 A1 | 2/2005 | McClelland |
| 2005/0117683 A1 | 6/2005 | Mishin |
| 2005/0117700 A1 | 6/2005 | Peschmann |
| 2005/0135668 A1 | 6/2005 | Polichar |
| 2005/0156734 A1 | 7/2005 | Zerwekh |
| 2005/0157842 A1 | 7/2005 | Agrawal |
| 2005/0169421 A1 | 8/2005 | Muenchau |
| 2005/0226364 A1 | 10/2005 | Bernard |
| 2005/0251397 A1 | 11/2005 | Zanovitch |
| 2006/0115109 A1 | 6/2006 | Whitson |
| 2006/0274916 A1 | 12/2006 | Chan |
| 2006/0284094 A1 | 12/2006 | Inbar |
| 2007/0009088 A1 | 1/2007 | Edic |
| 2007/0085010 A1 | 4/2007 | Letant |
| 2007/0110215 A1 | 5/2007 | Hu |
| 2007/0172129 A1 | 7/2007 | Tortora |
| 2007/0194909 A1 | 8/2007 | Garfield |
| 2007/0210255 A1 | 9/2007 | Bjorkholm |
| 2007/0269005 A1 | 11/2007 | Chalmers |
| 2007/0280416 A1 | 12/2007 | Bendahan |
| 2007/0280502 A1 | 12/2007 | Paresi |
| 2007/0286337 A1 | 12/2007 | Wang |
| 2008/0044801 A1 | 2/2008 | Modica |
| 2008/0056432 A1 | 3/2008 | Pack |
| 2008/0211431 A1 | 9/2008 | Mishin |
| 2008/0304622 A1 | 12/2008 | Morton |
| 2011/0176660 A1 | 7/2011 | Morton |
| 2011/0216881 A1 | 9/2011 | Modica |
| 2012/0177176 A1 | 7/2012 | Carver |
| 2013/0039472 A1 | 2/2013 | Morton |

FOREIGN PATENT DOCUMENTS

| | | |
|---|---|---|
| EP | 77018 | 4/1983 |
| EP | 0077018 A1 | 4/1983 |
| EP | 0176314 | 4/1986 |
| EP | 0261984 A2 | 3/1988 |
| EP | 0287707 | 10/1988 |
| EP | 0417965 | 3/1991 |
| EP | 0432568 | 6/1991 |
| EP | 0531993 A1 | 3/1993 |
| EP | 0584871 A1 | 3/1994 |
| EP | 0864884 A2 | 9/1998 |
| EP | 0919186 A2 | 6/1999 |
| EP | 0924742 A2 | 6/1999 |
| EP | 0930046 A2 | 7/1999 |
| EP | 0963925 A2 | 12/1999 |
| EP | 1277439 A1 | 1/2003 |
| EP | 1374776 A1 | 1/2004 |
| EP | 1413898 A1 | 4/2004 |
| EP | 2255224 | 12/2010 |
| FR | 2328280 A1 | 5/1977 |
| GB | 1497396 A | 1/1978 |
| GB | 1526041 A | 9/1978 |
| GB | 2015245 A | 9/1979 |
| GB | 2089109 A | 6/1982 |
| GB | 2212903 A | 8/1989 |
| GB | 2255634 A | 11/1992 |
| GB | 2277013 A | 10/1994 |
| GB | 2337032 A | 11/1999 |
| GB | 2404431 | 2/2005 |
| GB | 2409268 A | 6/2005 |
| GB | 2424065 A | 9/2006 |
| GB | 2437777 A | 11/2007 |
| GB | 2438317 A | 11/2007 |
| GB | 2470161 | 11/2010 |
| GB | 2470163 | 11/2010 |
| GB | 2470330 | 11/2010 |
| JP | 570175247 | 10/1982 |
| JP | 59016254 | 1/1984 |
| JP | 5975549 | 4/1984 |
| JP | 600015546 | 1/1985 |
| JP | 600021440 | 2/1985 |
| JP | H10211196 A | 8/1998 |
| JP | H11230918 A | 8/1999 |
| JP | 2001176408 | 6/2001 |
| JP | 2001233440 A | 8/2001 |
| JP | 2003126075 A | 5/2003 |
| JP | 2004000605 A | 1/2004 |
| JP | 2005013768 A | 1/2005 |
| WO | 9528715 A2 | 10/1995 |
| WO | 9802763 A1 | 1/1998 |
| WO | 9803889 A1 | 1/1998 |
| WO | 9820366 A1 | 5/1998 |
| WO | 9855851 A1 | 12/1998 |
| WO | 9939189 A2 | 8/1999 |
| WO | 9960387 A2 | 11/1999 |
| WO | 0033060 A2 | 6/2000 |
| WO | 0159485 | 8/2001 |
| WO | 03051201 A2 | 6/2003 |
| WO | 03105159 | 12/2003 |
| WO | 2004010127 A1 | 1/2004 |
| WO | 2004037088 | 5/2004 |
| WO | 2004111625 | 12/2004 |
| WO | 2005084351 | 9/2005 |
| WO | 2005091227 | 9/2005 |
| WO | 2005098400 A2 | 10/2005 |
| WO | 2006036076 A1 | 4/2006 |
| WO | 2006045019 | 4/2006 |
| WO | 2006078691 A2 | 7/2006 |
| WO | 2006095188 | 9/2006 |
| WO | 2006135586 | 12/2006 |
| WO | 2007035359 A2 | 3/2007 |
| WO | 2007051092 | 5/2007 |
| WO | 2007055720 A2 | 5/2007 |
| WO | 2007068933 A1 | 6/2007 |
| WO | 2007103216 A2 | 9/2007 |
| WO | 2008/017983 * | 2/2008 |
| WO | 2008017983 A2 | 2/2008 |
| WO | 2009027667 A2 | 3/2009 |
| WO | 2009088706 | 9/2009 |
| WO | 2009106803 | 9/2009 |
| WO | 2009106815 | 9/2009 |
| WO | 2009106857 | 9/2009 |
| WO | 2009141613 | 11/2009 |
| WO | 2009141615 | 11/2009 |

(56) References Cited

FOREIGN PATENT DOCUMENTS

| WO | 2009137698 | 12/2009 |
| WO | 2009150416 A2 | 12/2009 |
| WO | 2010135620 | 11/2010 |
| WO | 2011008718 | 1/2011 |
| WO | 2011069024 A1 | 6/2011 |
| WO | 2011087861 | 7/2011 |
| WO | 2011095810 | 8/2011 |
| WO | 2012109273 | 8/2012 |
| WO | 2012174265 | 12/2012 |

OTHER PUBLICATIONS

International Search Report for PCT/GB2009/000497, Jan. 22, 2010.
International Search Report for PCT/GB2009/000556, Feb. 19, 2010, Rapiscan Security Products, Inc.
International Search Report PCT/GB2009/000515, Feb. 23, 2010, Rapiscan Security Products, Inc.
International Search Report PCT/GB2009/001277, Jul. 20, 2010, Rapiscan Systems, Inc.
International Search Report PCT/GB2009/001444, Apr. 6, 2010, Rapiscan Security Products.
Mobile X-Ray Inspection Systems, Internet Citation, Feb. 12, 2007, pp. 1-2, URL:http://web.archive.org/web/20070212000928/http://www.bombdetecti-on.com/cat—details.php?catid=20.
Molchanov P A et al: 'Nanosecond gated optical sensors for ocean optic applications' Sensors Applications Symposium, 2006. Proceedings of the 2006 IEEE Houston, Texas,USA Feb. 7-9, 2006, Piscataway, NJ, USA,IEEE, Feb. 7, 2006, pp. 147-150, XP010917671 ISBN: 978-0-7803-9580-0.
Office Action dated Dec. 4, 2014 for U.S. Appl. No. 13/168,440.
Office Action dated May 20, 2015 for U.S. Appl. No. 13/168,440.
International Search Report for PCT/US2008/087654, date of mailing, Jul. 6, 2009, Rapiscan Security Products, Inc.
International preliminary report on patentability PCT/US2012/024184, issued on Aug. 13, 2013, Rapiscan Systems Inc.
International Search Report PCT/US2012/024184, mailed on Jul. 27, 2012, Rapiscan Systems Inc.
International Search Report PCT/US2012/042493, mailed on Oct. 1, 2012, Rapiscan Systems Inc.
International Search Report for PCT/GB2009/001277, Jul. 20, 2010, Rapiscan Systems Inc.
International Search Report for PCT/US10/58809; Rapiscan Systems Inc.; Apr. 19, 2011.
International Search Report for PCT/GB2009/001250, Mar. 2, 2010, Rapiscan Security Products Inc.
International Search Report for PCT/US10/35720, date of mailing, Nov. 15, 2010, Rapiscan Security Products, Inc.
International Search Report for PCT/GB2009/001275, Jul. 24, 2009, Rapiscan Security Products Inc.
Smith C. R. et al: 'Application of 450 kV computed tomography to engine blocks with steel liners' Materials Evaluation vol. 65, No. 5, 2007, pp. 458-461, XP055108238.
International Search Report for PCT/US2010/041757, mailed on Oct. 12, 2010, Rapiscan Systems Inc.
International Bureau of WIPO, International Preliminary Report on Patentability, PCT/US2005/011382, dated Oct. 19, 2006, 7 pages.
Mertz, L.N., et al, "Rotational aperture synthesis for x rays", Journal. Optical Society of America, vol. 3, Dec. 1986, pp. 2167-2170.
International Preliminary Report on Patentability, PCT/US2012/024182, issued on Aug. 13, 2013, Rapiscan Systems Inc.
International Search Report, PCT/US2012/024182 mailed on Aug. 20, 2012, Rapiscan Systems Inc.
International Search Report for PCT/US2010/061908, mailed on Apr. 2, 2012, Rapiscan Systems, Inc.
International Search Report for PCT/GB2006/000859, mailed on May 19, 2006, Corus UK Ltd.
International Search Report for PCT/GB2011/050182, Dec. 28, 2011.
International Search Report for PCT/US11/21758; Jul. 7, 2011, Rapiscan Systems Inc.
International Search Report for PCT/GB2009/000575, Apr. 7, 2010, Rapiscan Security Products Inc.
International Search Report for PCT/US2007/005444, Oct. 29, 2007, Telesecurity Sciences, Inc.
International Search Report for PCT/GB2004/001747, Aug. 10, 2004, CXR Ltd.
International Search Report for PCT/US2006/11492, Oct. 11, 2007, United Technologies Corporation.
Rapiscan Security Products, Inc., Users Guide for Levels 1 and 2 Threat Image Protection (TIP) Users Manual, Jan. 12, 2001, document in general.
Rapiscan Security Products, Inc., Users Guide for Level 3 Threat Image Projection (TIP) System Manual, Aug. 4, 1999, document in general.
'Test and Evaluation Plan for Screener Proficiency Evaluation and Reporting System (SPEARS) Threat Image Projection' J.L.Fobes, Ph.D., et al. FAA, Dec. 1995.
'Revised Test and Evaluation Plan for Determining Screener Training Effectiveness' Brenda A. Klock, et al. FAA, Aug. 2000.
'Development and Validation of a Test of X-ray Screener Readiness' Eric C. Neiderman, Ph.D., et al. IEEE, 2000.
Viggo Butler and Robert W. Poole, Jr., Rethinking Checked-Baggage Screening, Reason Public Policy Institute, Policy Study 297, Jul. 2002.
McLay, Laura A., Jacobson, Sheldon H., and Kobza, John E., A multilevel passenger screening problem for aviation security, Naval Research Logistics (NRL), vol. 53, issue 3, pp. 183-197, 2006.
Sun Olapiriyakul and Sanchoy Das, Design and analysis of a two-stage security screening and inspection system, Journal of Air Transport Management, vol. 13, Issue 2, Mar. 2007, pp. 67-74.
Kelly Leone and Rongfang (Rachel) Liu, the key design parameters of checked baggage security screening systems in airports, Journal of Air Transport Management, vol. 11, Issue 2, Mar. 2005, pp. 69-78.
European Patent Office, International Search Report, International Application No. PCT/US99/28266, dated Sep. 6, 2000, 3 pages.
International Search Report, PCT/US2007/066936; dated: Sep. 30, 2008, 5 pages.
International Search Report, PCT/US1998/18642, dated Jul. 7, 1999, 4 pages.
International Search Report, PCT/US1999/028035, dated Sep. 15, 2000, 6 pages.
Written Opinion of the International Searching Authority, PCT/US2007/066936, dated Sep. 30, 2008, 7 pages.
Notice of Allowance dated Nov. 3, 2015 for U.S. Appl. No. 13/168,440.

\* cited by examiner

1

GANTRY SCANNER SYSTEMS

CROSS-REFERENCE TO RELATED APPLICATIONS

The present application is a continuation application of U.S. patent application Ser. No. 12/993,832, filed on Feb. 10, 2011 and entitled "Gantry Scanner Systems", which is a national stage application of PCT/GB2009/001277, filed on May 20, 2009, which relies on Great Britain Patent Application Number 0809110.0, filed on May 20, 2008, for priority.

FIELD OF THE INVENTION

The present invention relates to scanners and in particular to gantry scanner systems. It has particular application in cargo scanners, but can be used with scanners in other fields.

BACKGROUND OF THE INVENTION

There is a requirement to screen cargo items for the detection of illicit materials and devices. Today, the use of X-ray imaging for cargo inspection is becoming more widespread. Such systems are typically made from large welded steel fabrications and are complex and time consuming to install.

SUMMARY OF THE INVENTION

The present invention provides a gantry scanner system comprising a radiation source, detection means which may comprise a plurality of detectors and a support frame supporting the detection means. The support frame may include an elongate support member arranged to support the detection means. The support frame may comprise cable support means arranged to support power cables or signal cables connected to the detectors. The support frame may comprise cover means arranged to cover the support member, the cable support means and the detectors.

The support frame may comprise a plurality of said support members connected together. The support frame may preferably comprise two of said support members connected together at right angles to each other to form a vertical side and a horizontal top of the frame, and a further vertical section connecting one of the support members to a radiation source module. The radiation source module and one of the support members may be movably supported by support means and guide means may be provided to guide the gantry to move along a pre-determined path.

The support member may be of a constant H-shaped cross-section along its length and may comprise a central web and two side sections. The detectors are preferably mounted within a cavity formed by the central web and the two side sections and radiation absorbing means are preferably mounted on an opposite side of the central web to the detectors.

Cable support means may be located on the outer side of at least one of the side sections of the elongate support members and may comprise a cable support tube or conduit mounted on the support section by means of a plurality of tube support brackets. Cover means may comprise a plurality of removable cover sections which can each be removed to allow access to the detectors. A control system and power storage means may be arranged to be connectable to a power supply so that it can be recharged.

The present invention further provides a gantry scanning system comprising a gantry, a radiation source, radiation detectors, a control system and rechargeable power storage means mounted on the gantry, wherein the power storage means is arranged to be connectable to a power supply so that it can be recharged. The system may further comprise guide means defining a path along which the gantry can move, wherein the power storage means are arranged to be connectable to the power supply only when it is in one or more recharging positions on the path. Recharging means are preferably provided at each end of the path so that the power storage means can be recharged in each of two recharging positions.

The control system is also preferably arranged to transmit scan data, obtained by the scanner, wirelessly to a remote station for analysis. The remote station may include display means arranged to display an image generated from the scan data. Further, the control system may be arranged to receive control instructions wirelessly from a remote control station.

BRIEF DESCRIPTION OF THE DRAWINGS

Preferred embodiments of the present invention will now be described by way of example only, with reference to the accompanying drawings, wherein.

DETAILED DESCRIPTION OF THE INVENTION

In the following embodiment of the present invention, a low cost X-ray imaging system is provided which is simple to install and rapid to commission.

Figure 1:
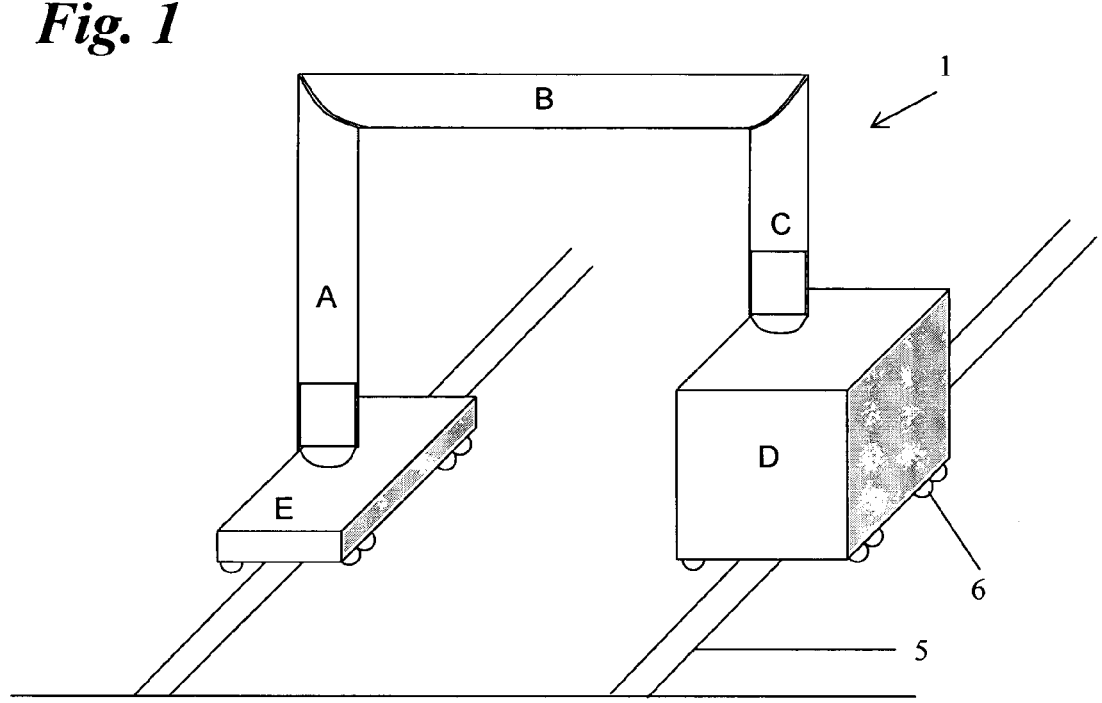
FIG. 1 is a perspective view of a gantry system according to an embodiment of the invention.

A plurality of elongate support members are connected together to form a gantry system as shown in FIG. 1. The gantry 1 comprises two vertical elongate support members A and C which are connected at their top ends at right angles to a horizontal elongate support member B to form an arch. The bottom end of each of the vertical members A and C is connected to and supported on a bogey E, D. One of the vertical support members A supports a multiplicity of individual X-ray detection elements. In a preferred embodiment, the horizontal member B also contains a multiplicity of individual X-ray detection elements. The other vertical support member C provides a structural function, and the bogey D on which it is supported contains the X-ray source, its associated power supplies and control system. The bogeys D and E enable motion of the gantry. The motion of the two bogeys E and D is controlled, such that the bogeys E and D move simultaneously at the same speed and in the same direction to move members A, B and C along rails 5.

In one embodiment, the imaging system is stationary and is operated as a portal. In this case there is no requirement to drive the imaging system backwards and forwards. In the embodiment shown, the imaging system is able to scan backwards and forwards under computer control around a stationary load under inspection. In another embodiment, the control system 44 in Section D is arranged to receive instructions from a remote station, thereby making the gantry 1 entirely wirelessly operated.

In the embodiment shown in FIG. 1, wheels 6 enable motion of the gantry and runners (not shown) located on the underside of bogeys D and E engage with rails 5 and allow movement of the gantry to keep the motion of the gantry uniform along the path defined by the rails 5.

Figure 2:
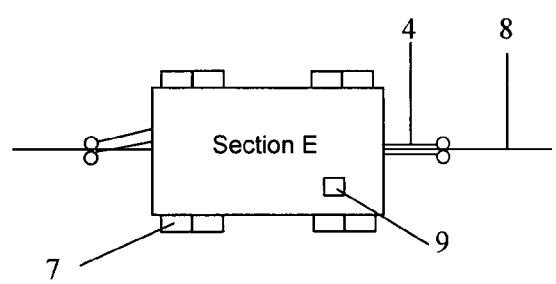
FIG. 2 is a plan view of a section of the gantry system of FIG. 1.

In an alternative embodiment, as shown in FIG. 2, small pneumatic wheels 7 are fitted to the underside of bogeys D and E that run on a level concrete floor. Mechanical guidance is achieved by a metal or plastic guide rail 8 which are fixed to the ground. In this example, a controlling system 9 receives feedback signals from a mechanical sensing arm 4 which is pivotally connected at one end to the bogey E and is engaged with the guide rail 8 at the other end so that it follows the guide rail 8. The control system processes the feedback signals which are indicative of the angle of the sensing arm and outputs instructions to a motor speed control circuit which controls the speed of the wheels 6 to prevent "crabbing" of the system whereby the unit goes off track. Here, the leftmost actuator is out of line, indicating a crabbing possibility.

In another embodiment, guide means defining a path along which the gantry can move are provided in the form of painted lines on the ground which are tracked by a video camera mounted on the bogey. Alternatively, magnetic strips are used which are tracked by a magnetic sensor mounted on the bogey. In yet another embodiment, wheels on bogey Sections E and D engage with rails. Alternative drive schemes may also be appropriate and will be apparent to a person skilled in the art.

Figure 3:
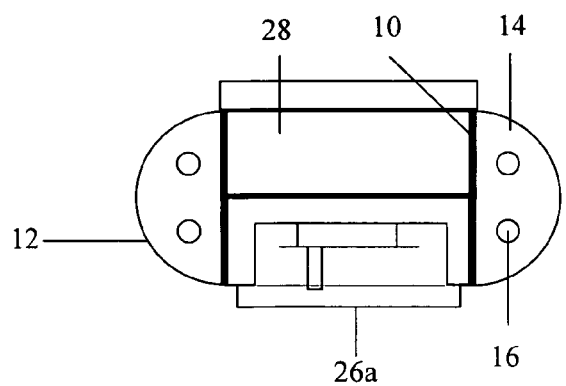
FIG. 3 is a cross-section of elongate support members A and B of FIG. 1.
Figure 3A:
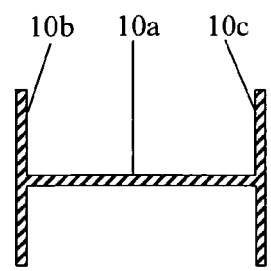
FIG. 3a is a cross-section of an H-shaped girder of FIG. 3.

As shown in FIGS. 3 and 3a, the elongate support members A, B and C are fabricated from a metal girder 10 with an H-shaped cross-section, which comprises a central web 10a and two side sections 10b, 10c. The girder 10 is intrinsically strong and of light weight and may be made of steel or aluminium. Alternatively a rigid composite material such as carbon fibre can be used. To provide further stiffness, an improved aerodynamic profile and weatherproofing, the girder 10 is enclosed by a skin 12, which is moulded carbon fibre composite, moulded glass fibre composite or pressed steel sheet which is welded or glued in place. As can be seen from FIG. 3, the skin surrounds part of the girder to form a generally rounded symmetric shape with one parallel section and two rounded ends. A long aperture 13 is formed in the outer skin 12 along the length of the support member to provide access to the detectors 34.

Figure 4:
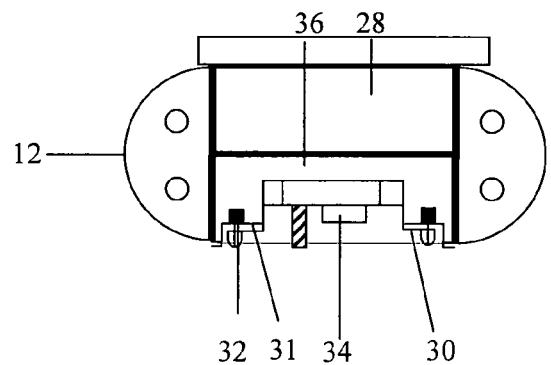
FIG. 4 is a cross-section of elongate support members A and B of FIG. 1 including a detector.

Referring to FIG. 4, X-ray detectors 34 are fitted within a cavity formed between the side sections 10b, 10c extending from a side of the central web 10a of the girder. A moulding 31 that would typically be formed separately to the outer skin 12 is affixed within the cavity on the side of the girder that is not covered by the outer skin One or more detectors 34 are pre-assembled into each metal or moulded plastic trays 30 which are then mounted onto the moulding 31 by fixing to pre-installed threaded inserts 32. It is advantageous to leave a gap 36 of uniform cross-section between the underside of the tray 30 and the moulding 31 filled with air in order to provide good thermal insulation of the detector components. It is also desirable to insert water absorbing materials, such as silica gel, into these spaces to provide longevity of the detectors 34. Radiation absorbing means 28, which may comprise a lead beam-stop, are mounted on the opposite side of the central web 10a to the detectors 34 between the side sections 10a, 10b.

Figure 5:
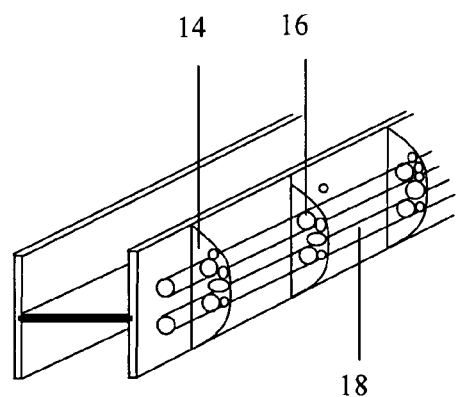
FIG. 5 is a schematic perspective view of the basic structure of elongate support members A, B and C.

The elongate support members A, B, C include support for cables. Prior to attachment of the outer skin 12, a series of thin steel support brackets 14 are welded to the girder 10. As shown in FIG. 5, each support bracket is semi-circular shaped and is affixed to the sides of sections 10b and 10c of the girder 10. The brackets 14 are perforated with holes 16 that have metal or plastic cable support tubes 18 or conduits inserted through them. The tubes 18 extend the full length of the elongate support members and each provide support for either power or signal cables, but not a mixture of power and signal cables. Typically two or three cable tubes 18 may be fitted per bracket 14.

Figure 6:
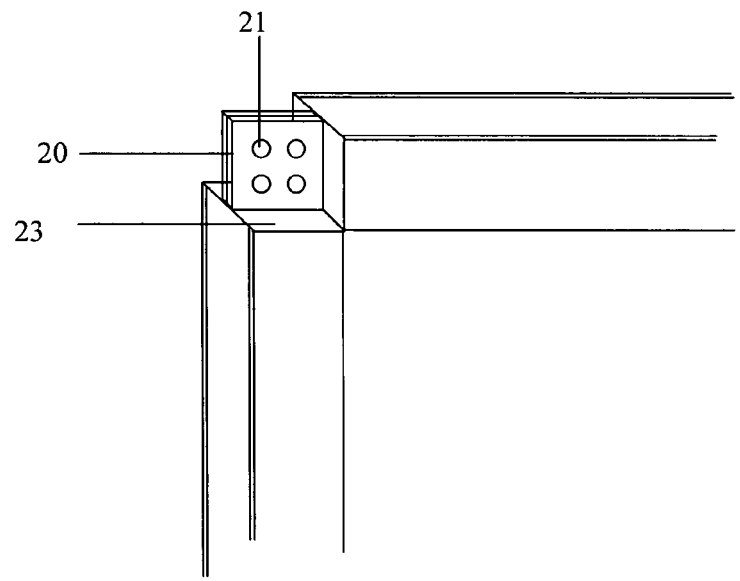
FIG. 6 is a schematic perspective view of a join between elongate support members A and B.

With reference to FIG. 6, an end plate 23 is fitted to the end of the girder of each of the support members A, B and C. A series of joining plates 20 are welded at right angles directly to the girder 10 at the end of Sections A, B and C to provide bolted joining points. Advantageously the joining plates 20 include alignment fixings 21 to ensure accurate assembly of the system prior to tightening up of the main bolts.

Figure 7:
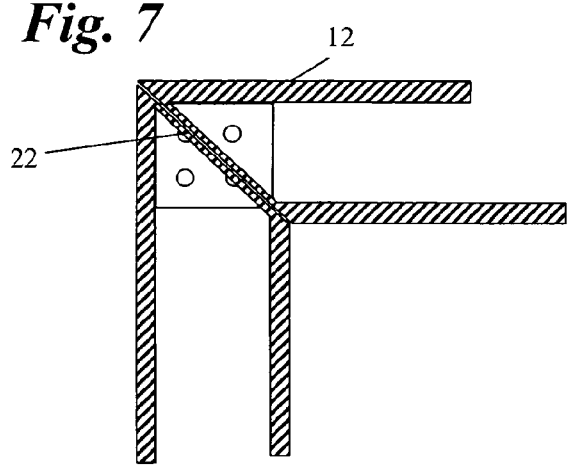
FIG. 7 is a sectional view of a join between elongate support members A and B of FIG. 1 showing the outer skin.
Figure 8:
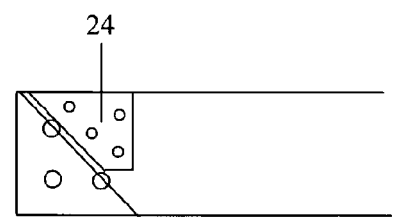
FIG. 8 is a side view of a removable access hatch on elongate support members A, B and C of FIG. 1.

A join between, for example, Sections A and B and between Sections B and C is weatherproofed as shown in FIG. 7. Here, the outer skin 12 at each end of the elongate support member is moulded such that it extends around the joining plate 20 and presents a large area flat face 22 which contacts with the equivalent end face of the other elongate support member when the system is assembled. One of the connecting faces is coated with a suitable adhesive, such as a silicone elastomer, prior to sealing with the other face. As shown in FIG. 8, a removable hatch 24 is provided in each elongate support section over the joint to allow access to the fixings 21 in the joining plates 20 and to allow routing of cables from the support brackets 14 in one of the support member A, B or C to those in the other. The removable hatch 24 is moulded to fit the curvature of the skin 12. The moulded hatch 24 and the skin 12 into which it fits is of a re-entrant design to prevent water ingress. Waterproofing is achieved by using a compressed elastic plastic foam which provides the final seal between the hatch 24 and skin 12. It is advantageous to use quick release fittings to fix the hatch 24 to the elongate support member to minimise repair and installation time. It is also advantageous to fill each of the sections between the outer skin 12 and the internal metal work with an expanded polyurethane foam or other suitable foam material in order to provide thermal insulation between the outer skin 12 and the components within the respective elongate support members A, B and C.

Figure 9A:
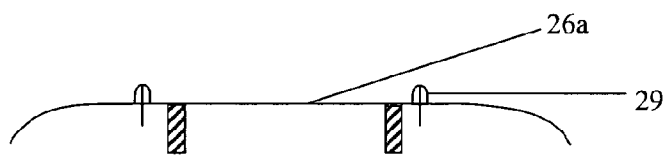
FIG. 9a is a schematic cross-section of a re-entrant cover of the system of FIG. 1.
Figure 9B:
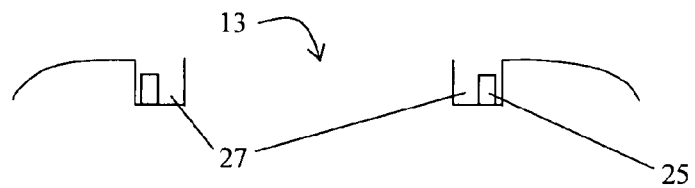
FIG. 9b is a schematic cross-section showing a part of an elongate support member of the system of FIG. 1 for receiving a re-entrant cover.
Figure 9C:
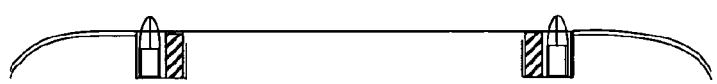
FIG. 9c is a schematic cross-section showing the re-entrant cover of FIG. 9a engaged to a section of a support member for receiving the re-entrant cover of FIG. 9b.

Weatherproof and light proof covers are required to protect the detectors 34 following installation. A re-entrant cover 26, shown in FIG. 9a, is appropriate for this purpose. As shown in FIG. 9b, channels 27 are formed in the skin 12 of the support members at the edge of the aperture 13. Fixtures 25 are located within the channels 27 and are arranged to receive the corresponding fixing 29 which projects down from the top surface 26a of the cover, as shown in FIG. 9a. Quick release fixings are used to allow rapid access for installation and service.

Figure 10:
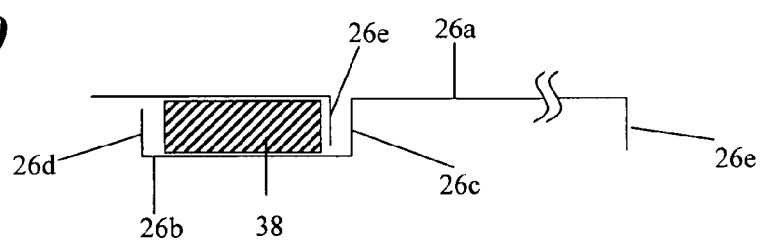
FIG. 10 is a longitudinal cross-section of a re-entrant cover along the length of an elongate support member of FIG. 1.
Figure 11:
FIG. 11 is a perspective view of a re-entrant cover along the length of an elongate support member of FIG. 1.

It is advantageous to use several small covers which overlap, as shown in FIG. 10, to allow rapid removal of the covers when access is required for installation or service purposes because it is easier for service personnel to manoeuvre small covers. Each cover has a substantially flat top surface 26a which is exposed when fitted, and a substantially flat lower surface 26b, spaced from the top surface by a vertical section 26c. A rim 26e projects downwards from one end of the top surface at right angles and a rim 26d projects upwards from the lower surface at right angles to form a trough along one end of the cover. An elastic plastic foam 38 is mounted on the underside the rim of the cover which is compressed when the covers are fitted to prevent environmental ingress. To retain strength, the covers have an arcuate form as shown in FIG. 11. In another embodiment, the cover is hinged along its long edge from fixings that are located on the outside of the outer skin.

Figure 12:
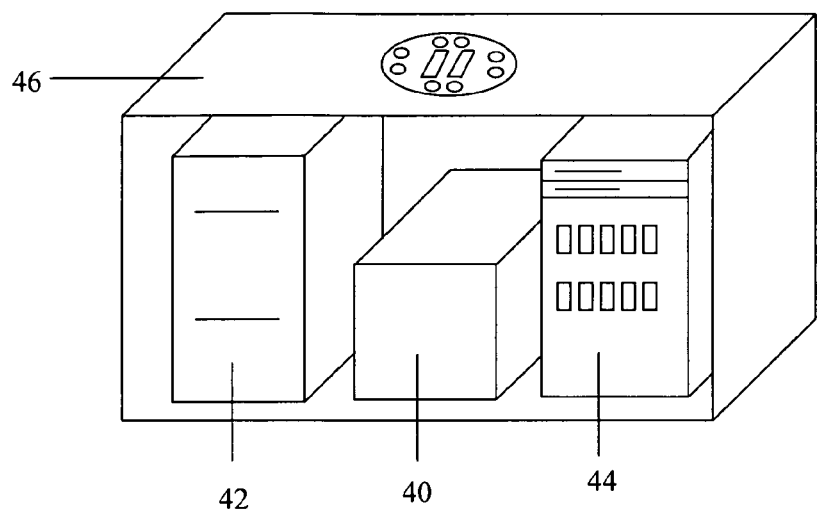
FIG. 12 is a perspective view of part of the gantry system of FIG. 1.
Figure 13:
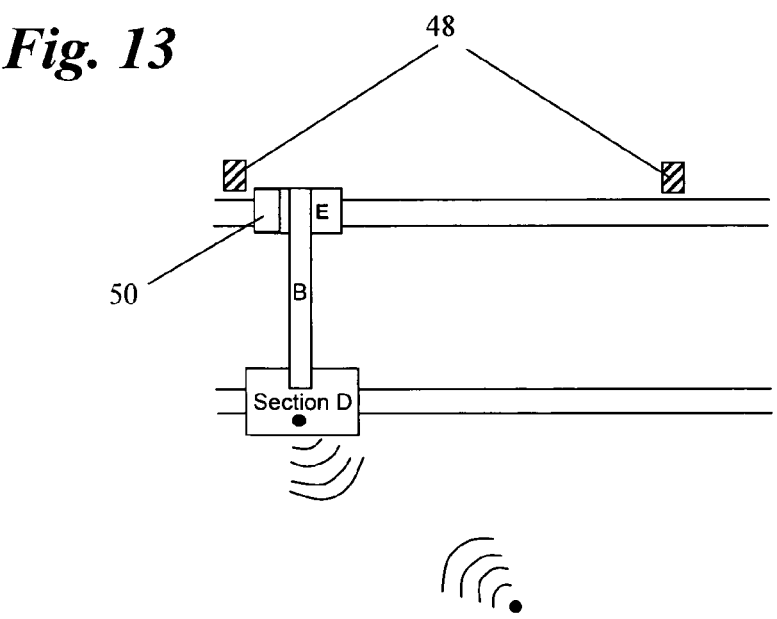
FIG. 13 is a plan view of the gantry system of FIG. 1 including an uninterruptible power supply according to a further embodiment of the invention.

Referring to FIG. 12, bogey D is a cabinet that contains an X-ray linear accelerator 40, an X-ray power supply 42 and control system 44. The cabinet is manufactured using a welded steel framework 46 suitable for supporting the weight of the various components to be installed, and is fitted with weatherproof doors which can be locked shut using keys.

A drawback of many conventional gantry systems is that power and data is typically handled using cables passed through a cable management system such as a caterpillar track system or a cateenery (suspended cable) system. In a preferred embodiment, the power supply 42 includes an uninterruptible power supply 50 (UPS). The control system 44 controls and manages the UPS 50. The UPS 50 is configured to receive mains power from docking stations 48 that are located at either end of the scanning region or guide path as shown in FIG. 12. While the gantry is adjacent to a docking station 48 at each of the two recharging positions, the control system is arranged to establish a connection between the UPS 50 and the docking station 48, in order to allow the power storage means 42 to recharge via the UPS 50. The gantry 1 is self powered while a scan is in progress and works successfully when the time that the system is scanning is less that the time that the system is charging. This is typically the case when individual cargo loads need to be positioned within the imaging zone prior to scanning The UPS 50 operates to receive power to be recharged only when the power supply 42 is in one or more recharging positions on the path along which the gantry 1 moves.

The control system 44 stores and manages all imaging data relating to each scan and converts the imaging data associated with each scan to an Ethernet packet for transmission wirelessly to a local network access point or to a remote station for analysis. An image generated from the scan data is displayed on a monitor for inspection at the remote station.

I claim:

1. A gantry scanner system comprising
a first housing;
a radiation source positioned in the first housing; and
a support frame attached to the first housing, wherein the support frame comprises
a first vertical section extending up from the first housing;
a first horizontal section attached to the first vertical section and extending outward therefrom; and
a second vertical section attached to the first horizontal section and extending downward therefrom, wherein at least one of the first horizontal section and second vertical section comprises a girder having an H-shaped cross section defined by a central horizontal member and two vertical side members, an outer skin comprising two sides, wherein each of said two sides is generally rounded and configured to cover one of said two vertical side members, a support structure positioned in a first cavity defined on each side by the central horizontal member and the two vertical side members, and a detector attached to the support structure, wherein the detector is separated from the central horizontal member by a space.

2. The gantry scanner system of claim 1 wherein the first horizontal section is attached to the first vertical section at a substantially 90 degree angle and wherein the first horizontal section is attached to the second vertical section at a substantially 90 degree angle.

3. The gantry scanner system of claim 1 further comprising a second cavity defined on each side by the central horizontal member and the two vertical side members, wherein the second cavity is different from the first cavity and a radiation absorbing means is positioned in said second cavity.

4. The gantry scanner system of claim 3 wherein the radiation absorbing means comprises a lead beam-stop.

5. The gantry scanner system of claim 1 further comprising a cable support tube mounted on the support frame by a plurality of tube support brackets.

6. The gantry scanner system of claim 1 further comprising a control system adapted to control a movement of the support frame.

7. The gantry scanner system of claim 6 wherein the detector is configured to generate scan data and wherein the control system is arranged to transmit the scan data wirelessly to a remote station for analysis.

8. The gantry scanner system of claim 1 further comprising a water absorbing material positioned in said space.

9. The gantry scanner system of claim 8 wherein the water absorbing material is silica gel.

10. The gantry scanner system of claim 1 wherein the outer skin comprises at least one of carbon fibre composite, glass fibre composite, and pressed steel sheet.

11. The gantry scanner system of claim 1 wherein the girder has an end and wherein a joining plate is attached to the end of the girder.

12. The gantry scanner system of claim 11 further comprising an alignment fixing positioned on said joining plate.

* * * * *